United States Patent
Shido et al.

(10) Patent No.: US 11,904,294 B2
(45) Date of Patent: Feb. 20, 2024

(54) CONCENTRATION DEVICE

(71) Applicant: Panasonic Intellectual Property Management Co., Ltd., Osaka (JP)

(72) Inventors: Chiaki Shido, Kyoto (JP); Hiroshi Ushio, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 902 days.

(21) Appl. No.: 16/959,967

(22) PCT Filed: Dec. 14, 2018

(86) PCT No.: PCT/JP2018/046140
§ 371 (c)(1),
(2) Date: Jul. 2, 2020

(87) PCT Pub. No.: WO2019/138783
PCT Pub. Date: Jul. 18, 2019

(65) Prior Publication Data
US 2021/0060524 A1 Mar. 4, 2021

(30) Foreign Application Priority Data
Jan. 15, 2018 (JP) .................. 2018-004570

(51) Int. Cl.
*B01J 20/24* (2006.01)
*C02F 1/28* (2023.01)
(Continued)

(52) U.S. Cl.
CPC ............... *B01J 20/24* (2013.01); *C02F 1/28* (2013.01); *C02F 1/44* (2013.01); *G01N 1/10* (2013.01)

(58) Field of Classification Search
CPC ..... B01J 20/24; C02F 1/28; C02F 1/44; C02F 1/445; C07K 1/14; C07K 1/34;
(Continued)

(56) References Cited

U.S. PATENT DOCUMENTS

| 6,129,828 A * | 10/2000 | Sheldon, III ........... C12N 13/00 |
| | | 204/615 |
| 2011/0318240 A1* | 12/2011 | Boone ................. G01N 33/573 |
| | | 422/402 |
| 2013/0337437 A1* | 12/2013 | Henze ................ G01N 33/5436 |
| | | 435/7.37 |

FOREIGN PATENT DOCUMENTS

JP   2012-249598 A   12/2012

OTHER PUBLICATIONS

JP2000246073A English translation, Japanese publication published (Year: 2002).*

(Continued)

*Primary Examiner* — Christine T Mui
*Assistant Examiner* — Jonathan Bortoli
(74) *Attorney, Agent, or Firm* — Rimon P.C.

(57) ABSTRACT

A concentration device that concentrates a solution containing a biological substance includes: a first chamber into which the solution is to be introduced; a second chamber to be filled with a drawing agent; and a film that separates a space of the first chamber and a space of the second chamber. The film has a first region and a second region. The first region is semipermeable in that the first region is permeable to a solvent of the solution but impermeable to the biological substance and the drawing agent. The second region is impermeable to the solution, the biological substance, and the drawing agent. When the solution is introduced into the first chamber, the film is positioned to incline with respect to a surface of the solution. The second region (Continued)

is positioned below the first region with respect to the surface of the solution.

13 Claims, 13 Drawing Sheets

(51) Int. Cl.
 *C02F 1/44* (2023.01)
 *G01N 1/10* (2006.01)
(58) Field of Classification Search
 CPC ........ G01N 1/10; G01N 1/4005; G01N 1/405; G01N 2001/4016; G01S 7/60; H03H 17/06; H04L 7/0058
 See application file for complete search history.

(56) References Cited

OTHER PUBLICATIONS

International Search Report issued in corresponding International Patent Application No. PCT/JP2018/046140, dated Feb. 26, 2019, with English translation.

\* cited by examiner

CONCENTRATION DEVICE

CROSS-REFERENCE OF RELATED APPLICATIONS

This application is the U.S. National Phase under 35 U.S.C. § 371 of International Patent Application No. PCT/JP2018/046140, filed on Dec. 14, 2018, which in turn claims the benefit of Japanese Application No. 2018-004570, filed on Jan. 15, 2018, the entire disclosures of which Applications are incorporated by reference herein.

TECHNICAL FIELD

The present disclosure relates to a concentration device for a solution containing one or more biological substances.

BACKGROUND ART

A biological sample includes a plurality of species of biological substances. Detecting these biological substances enables understanding of conditions of biological functions. Furthermore, only minute amounts of biological substances are included in a biological sample. Thus, in order to improve the sensitivity of detection, a solution including biological substances needs to be concentrated. For example, Patent Literature (PTL) 1 discloses a concentrator in which polyethylene glycol powder is enclosed between a cylindrical core member and cellophane. The disclosed concentrator efficiently concentrates a specimen solution using difference in osmotic pressure between polyethylene glycol and water.

CITATION LIST

Patent Literature

PTL 1: Japanese Unexamined Patent Application Publication No. 2012-249598

SUMMARY OF THE INVENTION

Technical Problem

The conventional technique disclosed in PTL 1 enables efficient concentration of the specimen solution by immersing the cylindrical concentrator in the specimen solution. However, the contact area between the cellophane and the specimen solution in the concentrator decreases as the amount of the specimen solution decreases, and this reduces the concentration efficiency.

In view of the above, the present disclosure provides a concentration device capable of efficiently concentrating a solution containing one or more biological substances.

Solution to Problem

A concentration device according to one aspect of the present disclosure includes: a first chamber into which the solution is to be introduced; a second chamber to be filled with a drawing agent; and a film that separates a space of the first chamber and a space of the second chamber. The film has a first region and a second region. The first region is semipermeable in that the first region is permeable to a solvent of the solution but impermeable to the biological substance and the drawing agent, the second region is impermeable to the solution, the biological substance, and the drawing agent. When the solution is introduced into the first chamber, the film is positioned to incline with respect to a surface of the solution, and the second region is positioned below the first region with respect to the surface of the solution.

Advantageous Effect of Invention

The present disclosure makes it possible to provide a concentration device capable of efficiently concentrating a solution containing one or more biological substances.

DESCRIPTION OF EXEMPLARY EMBODIMENTS

Figure 1:
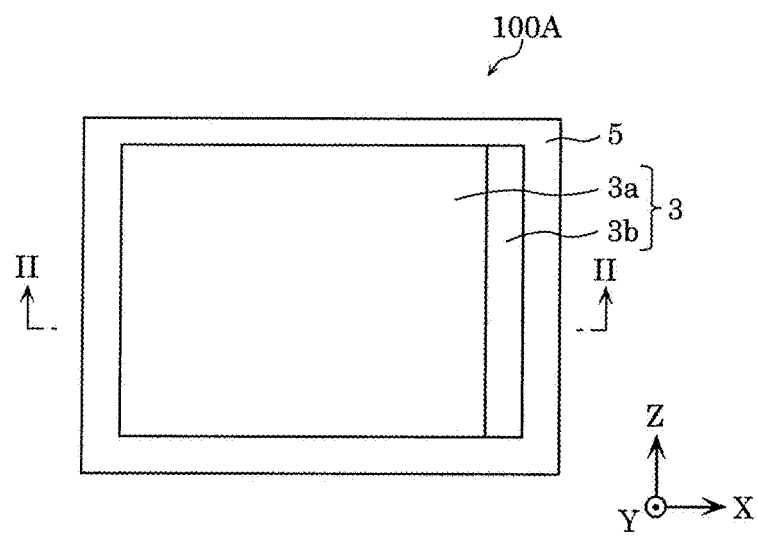
FIG. 1 is a top view of a concentration device according to Embodiment 1.

The following describes an overview of one aspect of the present disclosure.

A concentration device according to one aspect of the present disclosure includes: a first chamber into which the solution is to be introduced; a second chamber to be filled with a drawing agent; and a film that separates a space of the first chamber and a space of the second chamber. The film has a first region and a second region. The first region is semipermeable in that the first region is permeable to a solvent of the solution but impermeable to the biological substance and the drawing agent. The second region is impermeable to the solution, the biological substance, and the drawing agent. When the solution is introduced into the first chamber, the film is positioned to incline with respect to a surface of the solution, and the second region is positioned below the first region with respect to the surface of the solution.

Accordingly, when a solution containing a biological substance is introduced into the first chamber, the film is positioned to incline with respect to the surface of the solution. With this, the area of the solution that is in contact with the film can be kept large, regardless of the amount of the solution. With this, a solution containing a biological substance can be efficiently concentrated. Furthermore, the film has a second region, and the second region is positioned below the first region with respect to the surface of the solution. This suppresses depletion of the solution.

For example, in the concentration device according to one aspect of the present disclosure, the film may have a plurality of sides that define an external shape of the film in a top view, the plurality of sides may include a first segment that also serves as a side of the first region among the plurality of sides, and the plurality of sides may include a second segment that also serves as a side of the second region among the plurality of sides. The second segment may be shorter than the first segment.

With this, the area of the first region is larger than the area of the second region. Thus, the area of the solution containing a biological substance in contact with the first region can be increased, and thus the solution can be efficiently concentrated.

For example, in the concentration device according to one aspect of the present disclosure, the external shape of the film may be trapezoidal.

Accordingly, the area of the solution containing a biological substance in contact with the first region can be increased, and thus the solution can be efficiently concentrated.

For example, in the concentration device according to one aspect of the present disclosure, the film may have an axis of symmetry perpendicular to a direction in which first regions and second regions are aligned in a top view, the first regions each being the first region, the second regions each being the second region. The first regions and the second regions may be symmetrically positioned with respect to the axis of symmetry.

This further increases the area of the solution containing a biological substance in contact with the film, and thus the solution can be concentrated more efficiently.

For example, the concentration device according to one aspect of the present disclosure may further include a carrier that is placed on the second region in the first chamber and carries the biological substance.

Accordingly, a solution containing a biological substance can be adsorbed on the carrier while the solution containing a biological substance is concentrated. Thus, after the solution is concentrated, the concentrated liquid including the biological substance can be easily collected.

For example, in the concentration device according to one aspect of the present disclosure, the carrier may be a porous material.

Accordingly, a porous carrier can increase the surface area of the carrier. Thus, a larger amount of the biological substance can be carried.

For example, in the concentration device according to one aspect of the present disclosure, the porous material may be cellulose.

Cellulose has a significantly large specific surface area and high chemical stability, and thus cellulose adsorbs a larger amount of the biological substance more stably.

For example, in the concentration device according to one aspect of the present disclosure, the drawing agent may be liquid.

This enables the drawing agent to fill the second chamber completely.

For example, in the concentration device according to one aspect of the present disclosure, the drawing agent may be powder.

With this, the concentration device according to one aspect of the present disclosure can be stored and transported stably without changing its quality in a state in which power drawing agent is filled in the chamber as compared with when the drawing agent is liquid.

For example, the concentration device according to one aspect of the present disclosure may also have a shaker (not illustrated) that shakes the solution in the direction in which the film inclines.

This cyclically creates a period in which the solution comes into contact with a larger area of the first region. This results in a faster concentration of the solution, which further improves the concentration efficiency of the solution.

For example, the concentration device according to one aspect of the present disclosure may have an analyzer that separates the biological substance using the carrier.

With this, a solution containing the concentrated biological substance can be easily separated.

The embodiments according to the present disclosure are described in detail below, with reference to drawings.

Note that each of the embodiments described below shows a general or specific example. Numerical values, shapes, structural elements, the arrangement and connection of the structural elements, steps, the processing order of the steps, etc. shown in the following embodiments are mere examples, and are not intended to limit the scope of the present disclosure. Among the structural elements in the following embodiments, structural elements not recited in any one of the independent claims representing the broadest concepts are described as optional structural elements. Note that the figures are not necessarily precise depictions. Throughout the figures, structural elements that are essentially the same share like reference signs. Accordingly, duplicate description may be omitted or simplified.

Embodiment 1

[Overview of Concentration Device]

First, a concentration device according to the present embodiment will be described.

The concentration device according to the present embodiment concentrates a solution containing one or more biological substances (hereinafter, it may be simply referred to as a "solution").

The biological substances are substances that constitute an organism. Examples of the biological substances include high polymers such as proteins, nucleic acids, and polysaccharides; peptides; nucleotides; nucleosides; lipids; and amino acids.

Each of the biological substances has a function that works in an organism. By taking proteins as an example, keratin and collagen has a function of creating the structure of an organism and maintaining the strength of the structure. An enzyme has a function of being a catalyst of a reaction of an organism. An antibody has a function of protecting an organism. Separating such biological substances from biological samples such as blood, a mucosa, skin, and detecting the biological substances makes it possible to know states of these functions working in the organism, or consequently the condition of the organism (hereinafter, these states and condition are also referred to as a "biological condition").

The concentration device according to the present embodiment concentrates a solution containing one or more biological substances to facilitate detection of the biological substances for such a purpose, for example.

[Configuration of Concentration Device]

Figure 2:
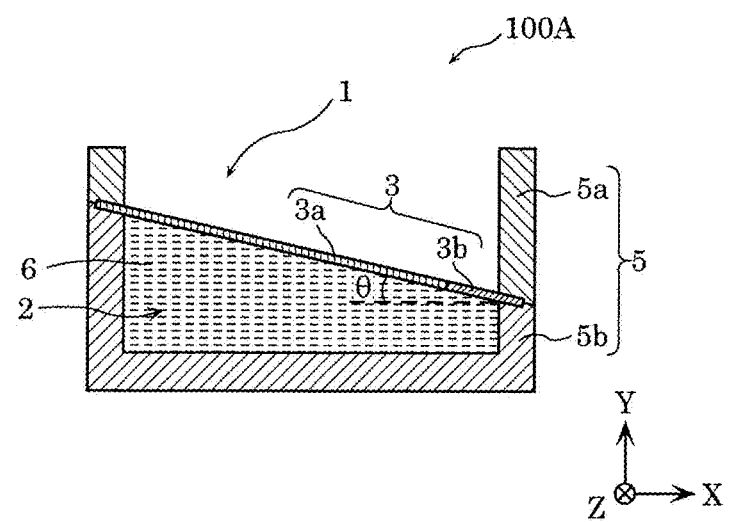
FIG. 2 is a schematic cross-sectional view taken along the line II-II in FIG. 1.

Next, the configuration of the concentration device according to the present embodiment will be described with reference to FIG. 1 and FIG. 2. FIG. 1 is a top view of concentration device 100A according to the present embodiment. FIG. 2 is a schematic cross-sectional view taken along the line II-II in FIG. 1.

As illustrated in FIG. 1 and FIG. 2, concentration device 100A has film 3 that vertically separates the space of chamber 5 having a bottom in the negative direction of the Y axis (hereinafter referred to as below). More specifically, as illustrated in FIG. 2, concentration device 100A includes first chamber 5a to which a solution is to be introduced, second chamber 5b in which drawing agent 6 is to be filled, and film 3 that separates space 1 of first chamber 5a and space 2 of chamber 5b. A solution containing one or more biological substances is introduced into first chamber 5a. Second chamber 5b is filled with drawing agent 6 that has an osmotic pressure higher than the osmotic pressure of the solution to be concentrated (here, a solution including one or more biological substances). Drawing agent 6 will be described in detail later.

Film 3 has first region 3a and second region 3b. First region 3a is semipermeable in that first region 3a is permeable to a solvent of the solution, but impermeable to the one or more biological substances and drawing agent 6. Second region 3b is impermeable to the solution, the one or more biological substances, and drawing agent 6.

First region 3a of film 3 is a membrane known as a semipermeable membrane. In general, a semipermeable membrane is a membrane that allows only a solvent such as water molecules to pass through it, but not a solute such as molecules or ions exceeding a predetermined size. Other than a solvent such as water molecules, the size of molecules or types of ions to pass through the membrane can be selected according to a desired design. In the present embodiment, first region 3a does not allow one or more target biological substances and drawing agent 6 to pass through it, and allows molecules and ions having a molecular weight less than the target biological substances and drawing agent 6 to pass through it. Examples of a material of first region 3a of film 3 include cellulose, polysulfone, and polyethersulfone.

Drawing agent 6 has an osmotic pressure higher than the osmotic pressure of a solution to be concentrated (here, a solution containing one or more biological substances). When drawing agent 6 and the solution containing one or more biological substances are made in contact with each other via first region 3a, which is a semipermeable membrane, a difference in osmotic pressure arises between drawing agent 6 and the solution. The solvent of the solution that is present on a side having a lower concentration of the solute, i.e., on a side having a lower osmotic pressure, permeates a side having a higher concentration of the solute, i.e., a side having a higher osmotic pressure. Theoretically, this phenomenon of permeation continues until the difference in osmotic pressure becomes zero. However, the present embodiment makes it possible to suppress depletion of the solution, because film 3 has second region 3b that is impermeable.

Drawing agent 6 is a substance that absorbs a solvent of the solution, i.e., has affinity for a solvent. In the present embodiment, drawing agent 6 may be a hydrophilic substance, for example. Furthermore, drawing agent 6 may be a substance having a large molecular weight, for example, a water-soluble polymer. As a water-soluble polymer, dextran, glycogen, polyethylene glycol, polyvinyl alcohol, or polyvinyl pyrrolidone may be used, for example. These water-soluble polymers may have a molecular weight in a range from 500 to 10,000,000, and may be in a range from 2,000 to 5,000,000.

Note that drawing agent 6 may be liquid or powder. When drawing agent 6 is liquid, drawing agent 6 can fill second chamber 5b completely. This increases the contact area between film 3 and drawing agent 6. Thus, this maintains a large area where the solvent of the solution passes through. Furthermore, when drawing agent 6 is powder, drawing agent 6 does not evaporate like liquid, even when concentration device 100A is stored in a state in which drawing agent 6 is filled in second chamber 5b. Thus, concentration device 100A can be stored stably without changing its quality during storage. Moreover, compared with when drawing agent 6 is liquid, drawing agent 6 is less likely to leak out of second chamber 5b during transportation when drawing agent 6 is powder. Thus, concentration device 100A can be transported stably without changing its quality during transportation. Other benefits regarding concentration obtained when drawing agent 6 is powder is that such drawing agent 6 can concentrate a larger amount of solution than when drawing agent 6 is liquid, because powder drawing agent 6 absorbs a larger amount of water of the solution than liquid drawing agent 6. Furthermore, because powder drawing agent 6 has a higher concentration of a solute than liquid drawing agent 6 does, the difference in osmotic pressure increases between powder drawing agent 6 and a solution containing one or more biological substances. Thus, the concentration speed of the solution increases. With this, a solution containing one or more biological substances can be concentrated faster, compared with when drawing agent 6 is liquid.

Moreover, drawing agent 6 may be filled in second chamber 5b of concentration device 100A in advance, or filled in second chamber 5b when concentration device 100A is used.

Note that in FIG. 1 and FIG. 2, a lid to be placed on the upper opening of chamber 5 is not illustrated. The concentration device may have a lid, or may be without a lid. When the concentration device does not have a lid, a component that can cover the opening of the chamber may be used. The form of the component that can cover the opening of the chamber is not particularly limited. Examples of the form the component include a plate, a sheet, a film, and a foil. The lid may also have an inlet for introducing the solution into the chamber. The size of the inlet may be appropriately determined according to the design of the concentration device.

Film 3 is positioned to incline with respect to the surface of the solution when the solution is introduced into first chamber 5a. Here, the inclination angle of film 3 is set to θ degrees. Accordingly, because film 3 is positioned to incline with respect to the surface of the solution, the contact area between the solution and film 3 increases. Thus, the area of the solution in contact with first region 3a of film 3 increases, thereby increasing the concentration efficiency of the solution.

Furthermore, second region 3b is positioned below first region 3a with respect to the surface of the solution. Accordingly, when second region 3b, which is impermeable, is positioned below first region 3a and the surface of the solution reaches second region 3b as the concentration proceeds, the concentration of the solution stops. Therefore, this suppresses depletion of the solution.

With this structure, concentration device 100A according to the present embodiment efficiently concentrates a solution containing one or more biological substances.

[Method of Concentrating Solution]

Next, a method of concentrating a solution using concentration device 100A according to the present embodiment will be described.

Figure 3:
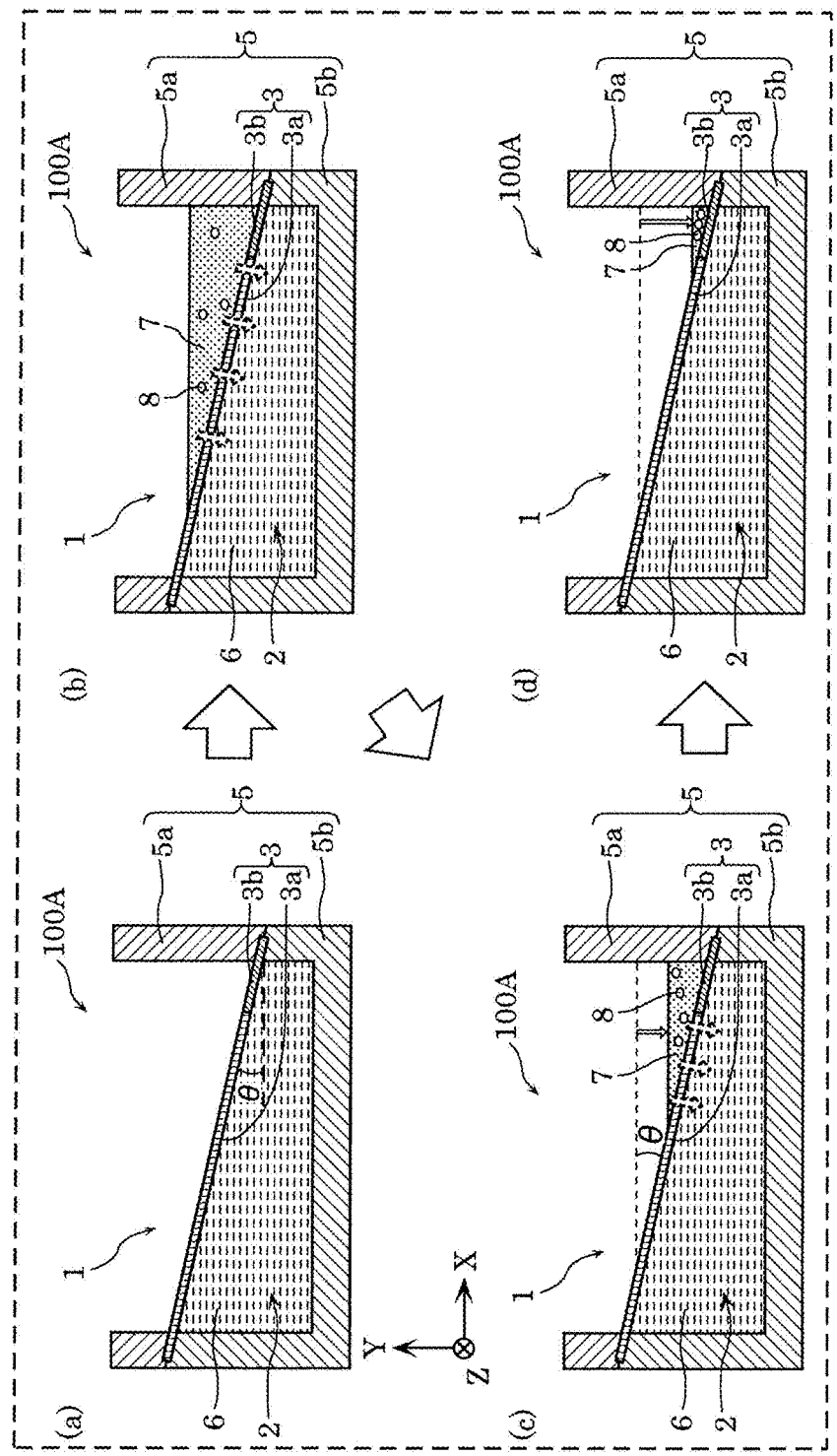
FIG. 3 is a diagram illustrating a process of a method of concentration.

FIG. 3 is a diagram illustrating a process of the method of concentration. As shown in (a) in FIG. 3, second chamber 5b of concentration device 100A is filled with drawing agent 6. Then, as shown in (b) in FIG. 3, solution 7 containing one or more biological substances 8 is introduced into first chamber 5a. At this time, when concentration device 100A has a lid, solution 7 may be introduced from the inlet of the lid. When concentration device 100A does not have a lid, a covering component may be placed on the opening of first chamber 5a after solution 7 is introduced into first chamber 5a. Examples of the covering component include materials having forms such as a film, a foil, a sheet, and a plate. Subsequently, as illustrated in (c) in FIG. 3, the solvent of solution 7 is absorbed into drawing agent 6, which is filled in second chamber 5b, via first region 3a of film 3. After that, as illustrated in (d) in FIG. 3, when solution 7 is concentrated to an amount that the surface of solution 7 reaches second region 3b in the top view, solution 7 is less likely to be concentrated because solution 7 is less likely to be in contact with first region 3a. This makes it possible to obtain solution 7 concentrated to a desired concentration rate.

Note that in the process of the above method of concentration, concentration device 100A may be shaken in an X-axis direction. In this case, concentration device 100A may also have a shaker (not illustrated) that shakes solution 7 in the direction in which film 3 inclines. This shakes solution 7 in the inclination direction of film 3, thereby cyclically creating a period in which solution 7 becomes in contact with first area 3a in a larger area. This results in a faster concentration of solution 7, further improving the concentration efficiency of solution 7.

Variation 1 of Embodiment 1

Figure 4:
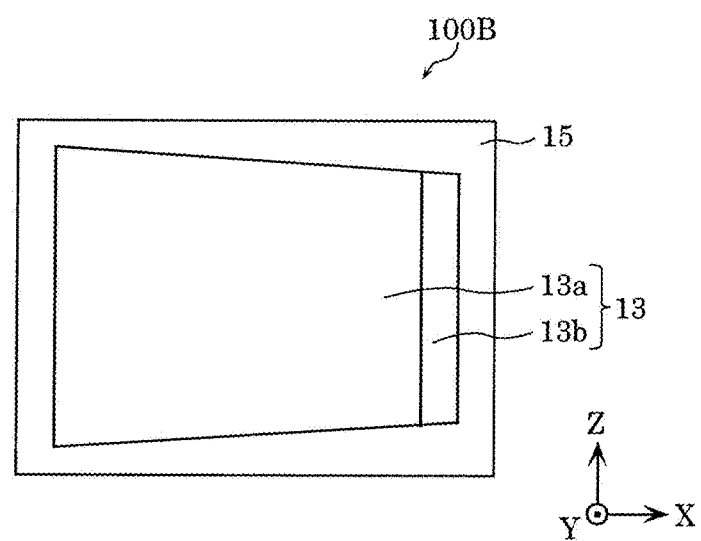
FIG. 4 is a top view of a concentration device according to Variation 1 of Embodiment 1.

Next, a concentration device according to Variation 1 of Embodiment 1 will be described. FIG. 4 is a top view of concentration device 100B according to the present variation.

In concentration device 100B according to the present variation, film 13 has a plurality of sides defining its external shape in a top view. The plurality of sides include a first segment that also serves as a side of first region 13a, and a second segment that also serves as a side of second region 13b. Here, a second segment is shorter than a first segment.

Accordingly, in film 13, the ratio of the area of first region 13a to the area of second region 13b is greater than in Embodiment 1. Thus, compared with the case in Embodiment 1, the area of solution 7 in contact with first region 13a can be increased when the same amount of solution 7 as the solution in concentration device 100A is introduced into concentration device 100B. Thus, solution 7 can be further efficiently concentrated.

As a specific example of such film 13, the external shape of film 13 is trapezoidal, as illustrated in FIG. 4. In concentration device 100B, the first segments are three segments other than one segment which is the boundary between first region 13a and second region 13b. Furthermore, the second segments are three segments other than one segment which is the boundary between first region 13a and second region 13b. In concentration device 100B, each of the second segments is shorter than any one of the first segments.

With this structure, the area of first region 13a is larger than the area of second region 13b of concentration device 100B. Thus, the area of the solution containing one or more biological substances in contact with first region 13a can be increased, and thus the solution can be efficiently concentrated.

Variation 2 of Embodiment 1

Figure 5:
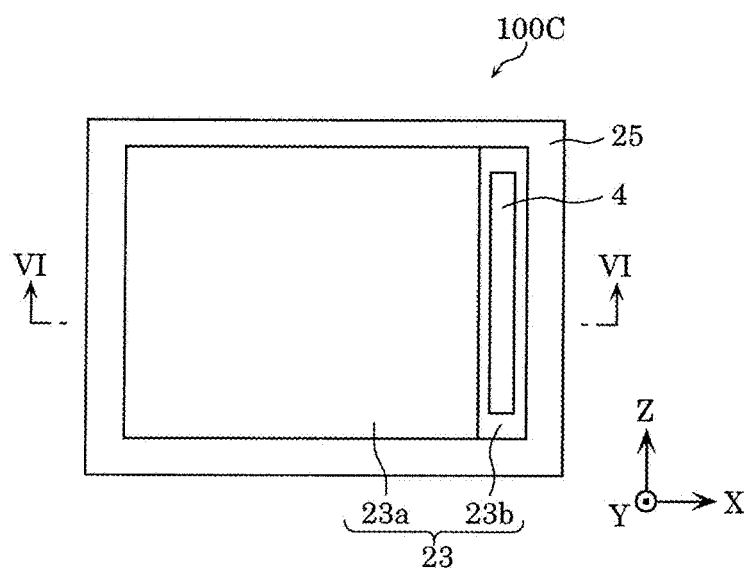
FIG. 5 is a top view of a concentration device according to Variation 2 of Embodiment 1.
Figure 6:
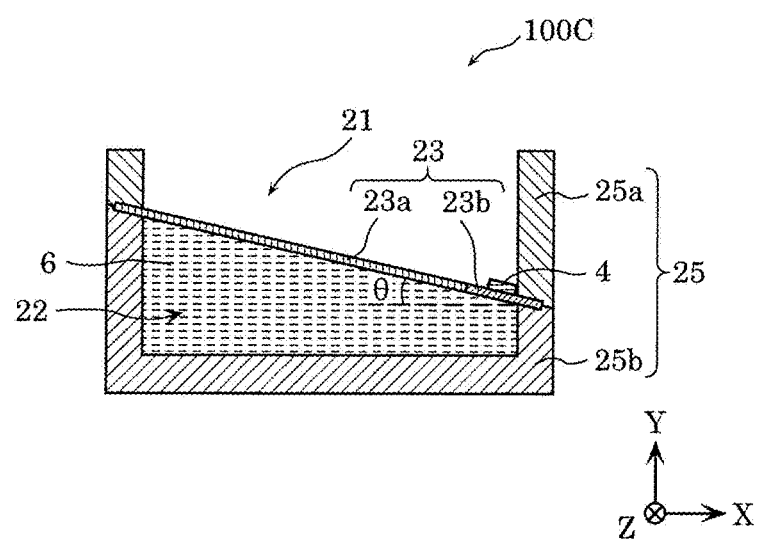
FIG. 6 is a schematic cross-sectional view taken along the line VI-VI in FIG. 5.

The following describes a concentration device according to Variation 2 of Embodiment 1. FIG. 5 is a top view of concentration device 100C according to the present variation. FIG. 6 is a schematic cross-sectional view taken along the line VI-VI in FIG. 5.

As illustrated in FIG. 5, concentration device 100C has film 23 that vertically separates the space of chamber 25 having a bottom below.

More specifically, as illustrated in FIG. 6, concentration device 100C includes first chamber 25a to which a solution is to be introduced, second chamber 25b in which drawing agent 6 is to be filled, and film 23 that separates space 21 of first chamber 25a and space 22 of chamber 25b. Film 23 has first region 23a and second region 23b. Film 23 is positioned with an inclination angle of θ degrees.

In addition, concentration device 100C according to the present variation has carrier 4 on second region 23b in first chamber 25a. Carrier 4 carries one or more biological substances. In this regard, concentration device 100C differs from concentration devices 100A and 100B described above.

Concentration device 100C includes carrier 4 that carries one or more biological substances on second region 23b. This allows the carrier to carry the biological substances while solution 7 is being concentrated. This reduces the effort to collect the concentrated solution, and suppresses reduction in the yield of one or more biological substances that may occur in collecting the concentrated solution, compared with when carrier 4 is not included.

Carrier 4 adsorbs and holds one or more biological substances on its surface or inside. Here, adsorption refers to a phenomenon that occurs between substances or molecules contained in the liquid phase and the surface of the solid phase, and occurs between the solid phase and the liquid phase. Adsorption is, for example, physical adsorption due to Van der Waals force. Here, it is relatively weak adsorption which can be irreversibly adsorbed and desorbed by controlling the temperature, pH, pressure, etc.

Note that carrier 4 may be a porous material. Carrier 4 being a porous material increases the surface area of carrier 4. This allows carrier 4 to adsorb a larger amount of one or more biological substances. Here, a porous material is a material having holes that are distributed evenly to some extent in at least one direction, and is not a material having holes that are unevenly distributed and distributed in only part of the material. For example, carrier 4 being a porous material means that the holes in carrier 4 are evenly distributed in the direction perpendicular to the thickness direction of carrier 4.

Examples of the porous material include the following: organic polymers represented by polyvinyl compounds such as polyethylene, polypropylene, polyvinyl chloride, polyacrylonitrile, polyacrylate, polymethacrylate, and polycarbonate; copolymers such as polystyrene latex, nylon, and polyterephthalate; inorganic materials such as glass, silica, and dirconia; and biological polymers such as cellulose, dextran, agarose, cellulose, and Sepharose (registered trademark). In particular, the porous material may be cellulose.

In addition, concentration device 100C according to the present variation may have an analyzer that separates one or more biological substances using carrier 4 on which the biological substances are adsorbed. In this way, concentration device 100C having the analyzer allows the biological substances to be easily separated after the solution has been concentrated, for example, by placing carrier 4 in the analyzer. Here, separation may be only fractionating a plurality of types of substances according to their characteristics, or may include identifying each substance or classifying each substance as a group of similar substances.

Note that "using carrier 4 on which one or more biological substance is adsorbed" means, for example, to isolate or separate the one or more biological substances by placing carrier 4 in the analyzer after the concentration is completed, and to extract the adsorbed biological substances from carrier 4 and separate the extracted biological substances with the analyzer. Examples of the separation method that can be performed in the analyzer include the following: thin-layer chromatography, ion-exchange chromatography, gel filtration, affinity chromatography, reversed-phase high-speed liquid chromatography (HPLC), mass spectrometry, fluorescence luminescence measurement, electrophoresis, and immunoassay. The separation method may be selected appropriately according to the types of the biological substances to be separated.

Accordingly, the concentration device according to the present embodiment efficiently concentrates a solution containing one or more biological substances.

Embodiment 2

Figure 7:
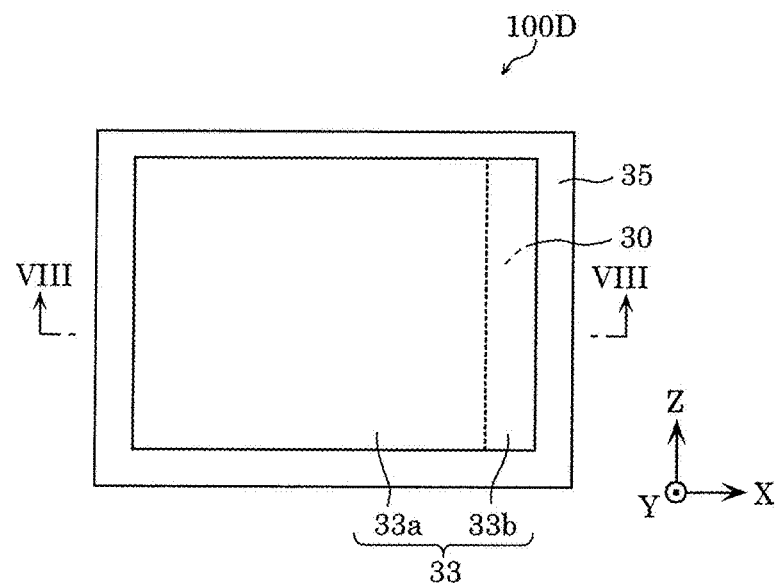
FIG. 7 is a top view of a concentration device according to Embodiment 2.
Figure 8:
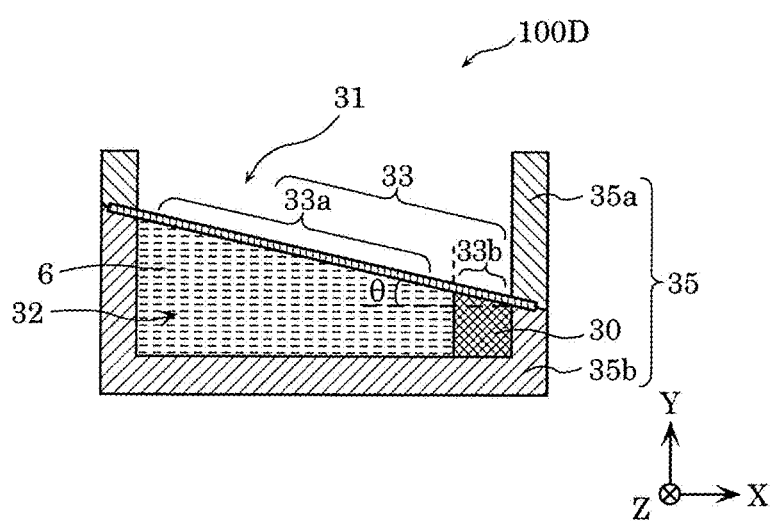
FIG. 8 is a schematic cross-sectional view taken along the line VIII-VIII in FIG. 7.

A concentration device according to Embodiment 2 will be described. FIG. 7 is a top view of concentration device 100D according to the present embodiment. FIG. 8 is a schematic cross-sectional view taken along the line VIII-VIII in FIG. 7.

The following describes differences from the concentration devices according to Embodiment 1 and its variations.

In concentration device 100D according to the present embodiment, film 33 is semipermeable in that film 33 is permeable to a solvent of a solution, but impermeable to one or more biological substances and the drawing agent.

In the present embodiment, film 33 itself does not have a semipermeable first region and an impermeable second region. Instead, second region 33b is a region where film 33 is in contact with prevention component 30, and first region 33a is a region where film 33 is not in contact with prevention component 30.

Prevention component 30 prevents drawing agent 6, which has a higher osmotic pressure, from being in contact with the solution containing one or more biological substances via film 33, which is a semipermeable membrane. If the solution containing drawing agent 6 having a high osmotic pressure does not come into contact with the solution containing one or more biological substances via film 33, the solvent is less likely to pass through film 33. As a result, prevention component 30 prevents drawing agent 6 from coming into contact with a region of film 33 corresponding to second region 33b. Note that prevention component 30 may be hollow. Also, prevention component 30 may be a component that covers a portion that is in contact with the under surface of film 33, or may be a wall component that separates space 32 of second chamber 35b along the boundary between first region 33a and second region 33b.

Variation 1 of Embodiment 2

Figure 9:
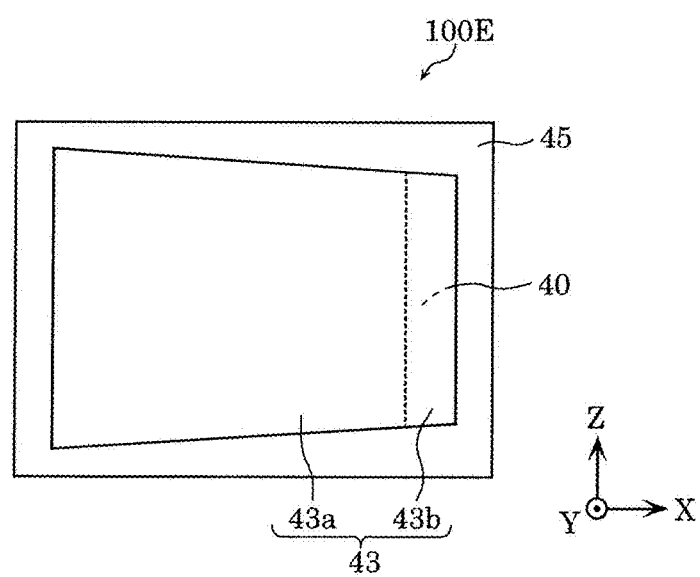
FIG. 9 is a top view of a concentration device according to Variation 1 of Embodiment 2.

First, a concentration device according to Variation 1 of Embodiment 2 will be described. FIG. 9 is a top view of concentration device 100E according to the present variation.

The following describes differences from concentration device 100D according to Embodiment 2. As illustrated in FIG. 9, film 43 of concentration device 100E has a trapezoidal external shape as described in Variation 1 of Embodiment 1. Also in the present variation, such a trapezoidal external shape of film 43 increases the area of the solution containing one or more biological substances in contact with first region 43a compared with concentration device 100D, when the same amount of solution as the solution in concentration device 100D is introduced into concentration device 100E. As a result, concentration device 100E concentrates a solution containing one or more biological substances more efficiently than concentration device 100D does.

Embodiment 3

Figure 10:
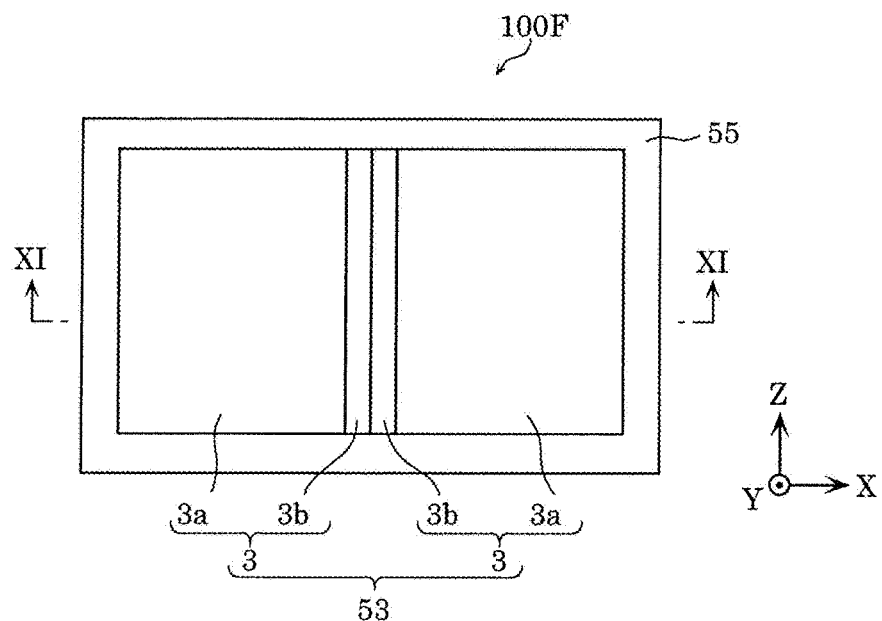
FIG. 10 is a top view of a concentration device according to Embodiment 3.
Figure 11:
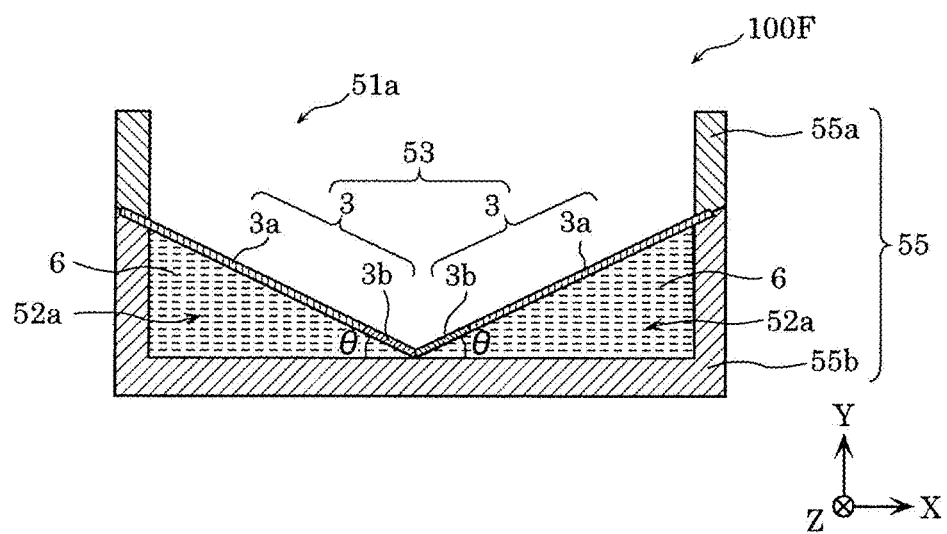
FIG. 11 is a schematic cross-sectional view taken along the line XI-XI in FIG. 10.

A concentration device according to Embodiment 3 will be described. FIG. 10 is a top view of concentration device 100F according to the present embodiment. FIG. 11 is a schematic cross-sectional view along the line XI-XI in FIG. 10.

The following describes differences from the concentration devices according to Embodiments 1 and 2.

As illustrated in FIG. 10, in concentration device 100F according to the present embodiment, film 53 has an axis of symmetry perpendicular to a direction in which first regions 3a and second regions 3b are aligned in the top view, and first regions 3a and second regions 3b are symmetrically positioned with respect to the axis of symmetry This further increases the area of a solution containing one or more biological substances in contact with film 53 in concentration device 100F, and thus the solution can be concentrated more efficiently. Furthermore, when concentration device 100F has a shaker (not illustrated), the shaker shakes the solution in a direction parallel to the alignment direction of first regions 3a and second regions 3b, for example. Thus, a period in which the solution comes into contact with first area 3a in a larger area can be created in a shorter cycle.

Moreover, as illustrated in FIG. 11, concentration device 100F includes film 53 that is positioned to vertically separate the space in chamber 55 into space 51a and space 52a. Film 53 includes two films 3 as shown in FIG. 10 and FIG. 11. The two films 3 are arranged so that ends of second regions 3b are in contact with each other—more specifically, so that the ends opposite the ends adjacent to first regions 3a are in contact with each other. With this, film 53 including two films 3 has the axis of symmetry, and first regions 3a and second regions 3b are symmetrically positioned with respect to the axis of symmetry in the top view. Moreover, the two films 3 are each positioned to incline with respect to the surface of the solution when the solution is introduced into first chamber 55a. Here, the inclination angles are set to θ degrees. In the present embodiment, spaces 52a in second chamber 55b are formed symmetrically with respect to the YZ plane including the axis of symmetry of film 53.

Variation 1 of Embodiment 3

Figure 12:
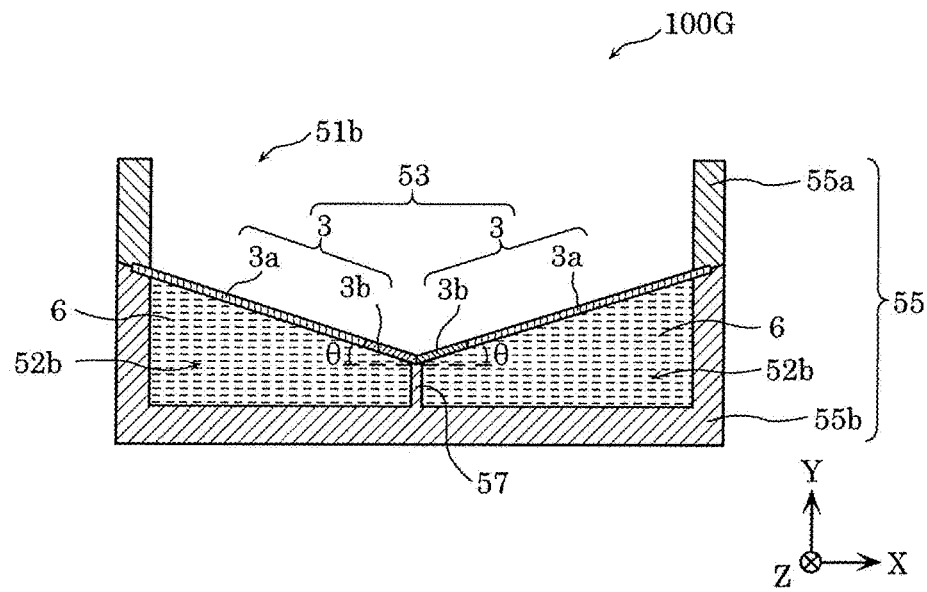
FIG. 12 is a schematic cross-sectional view of a concentration device according to Variation 1 of Embodiment 3.

Concentration device 100G according to Variation 1 of Embodiment 3 will be described. FIG. 12 is a schematic cross-sectional view taken along a plane parallel to the XY plane of concentration device 100G according to the present variation.

As illustrated in FIG. 12, concentration device 100G according to the present variation differs from concentration device 100F according to Embodiment 3 in that concentration device 100G includes support 57 along the axis of symmetry of film 53. Support 57 supports two films 3 along the axis of symmetry. This increases the volume of spaces 52b in second chamber 55b compared with concentration device 100F, thereby increasing the amount of drawing agent 6 t o be filled in second chamber 55b. Therefore, the amount of the solution to be concentrated can be increased.

Moreover, the volume ratio of the volume of spaces 52b in second chamber 55b to the volume of space 51b in first chamber 55a can be increased compared with concentration device 100F. This allows concentration device 100G to concentrate the solution to a higher concentration compared with concentration device 100F, even when the same combination of drawing agent 6 and the solution is introduced.

Variation 2 of Embodiment 3

Figure 13:
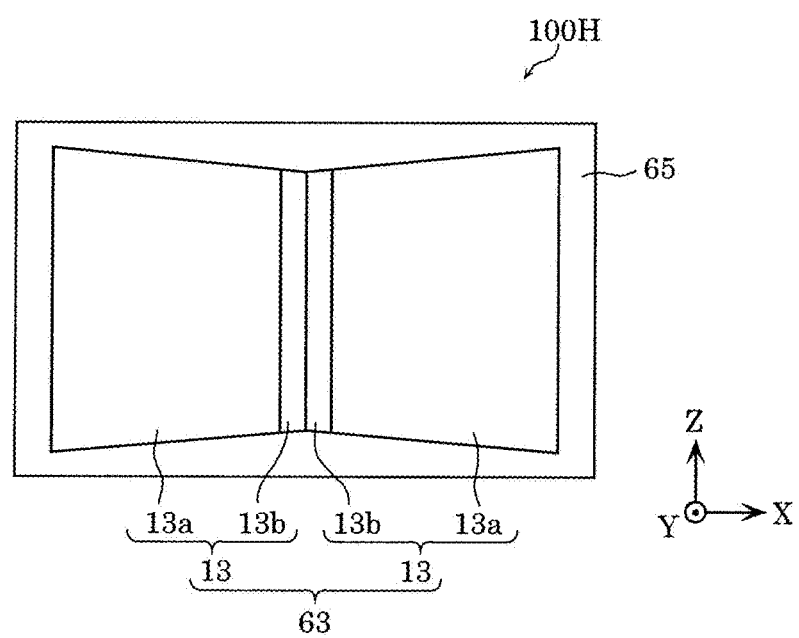
FIG. 13 is a top view of a concentration device according to Variation 2 of Embodiment 3.

A concentration device according to Variation 2 of Embodiment 3 will be described. FIG. 13 is a top view of concentration device 100H according to the present variation.

As illustrated in FIG. 13, concentration device 100H according to the present variation differs from concentration devices 100F and 100G in that the external shape of each of the two films 13 that make up film 63 is trapezoidal.

In the present variation, when each of the two films 13 has a trapezoidal external shape as described in Variation 1 of Embodiment 1, the area of the solution containing one or more biological substances in contact with first region 13a can be increased in concentration device 100H, compared with concentration devices 100F and 100G, when the same amount of solution as the solutions in concentration devices 100F and 100G is introduced into concentration device 100H. With this, the solution can be more efficiently concentrated.

Embodiment 4

Figure 14:
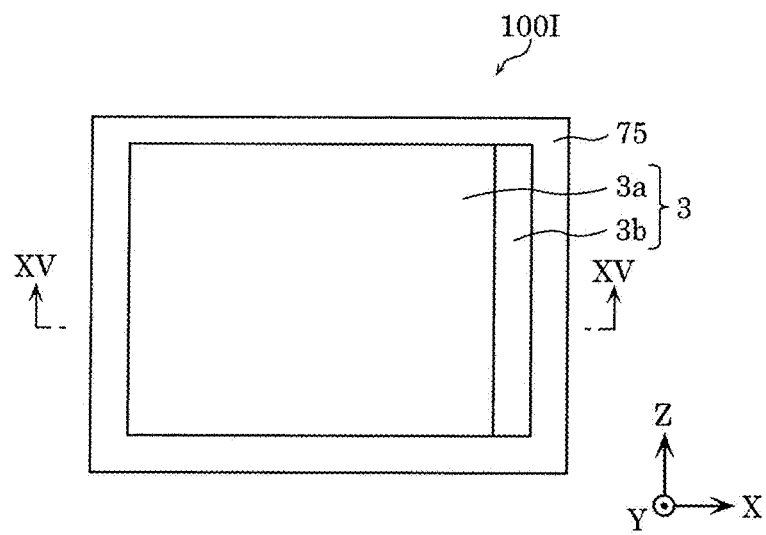
FIG. 14 is a top view of a concentration device according to Embodiment 4.
Figure 15:
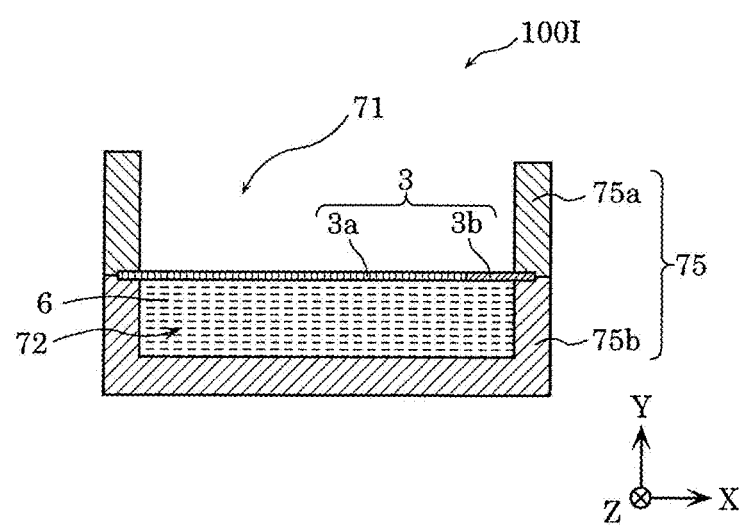
FIG. 15 is a schematic cross-sectional view taken along the line XV-XV in FIG. 14.
Figure 16:
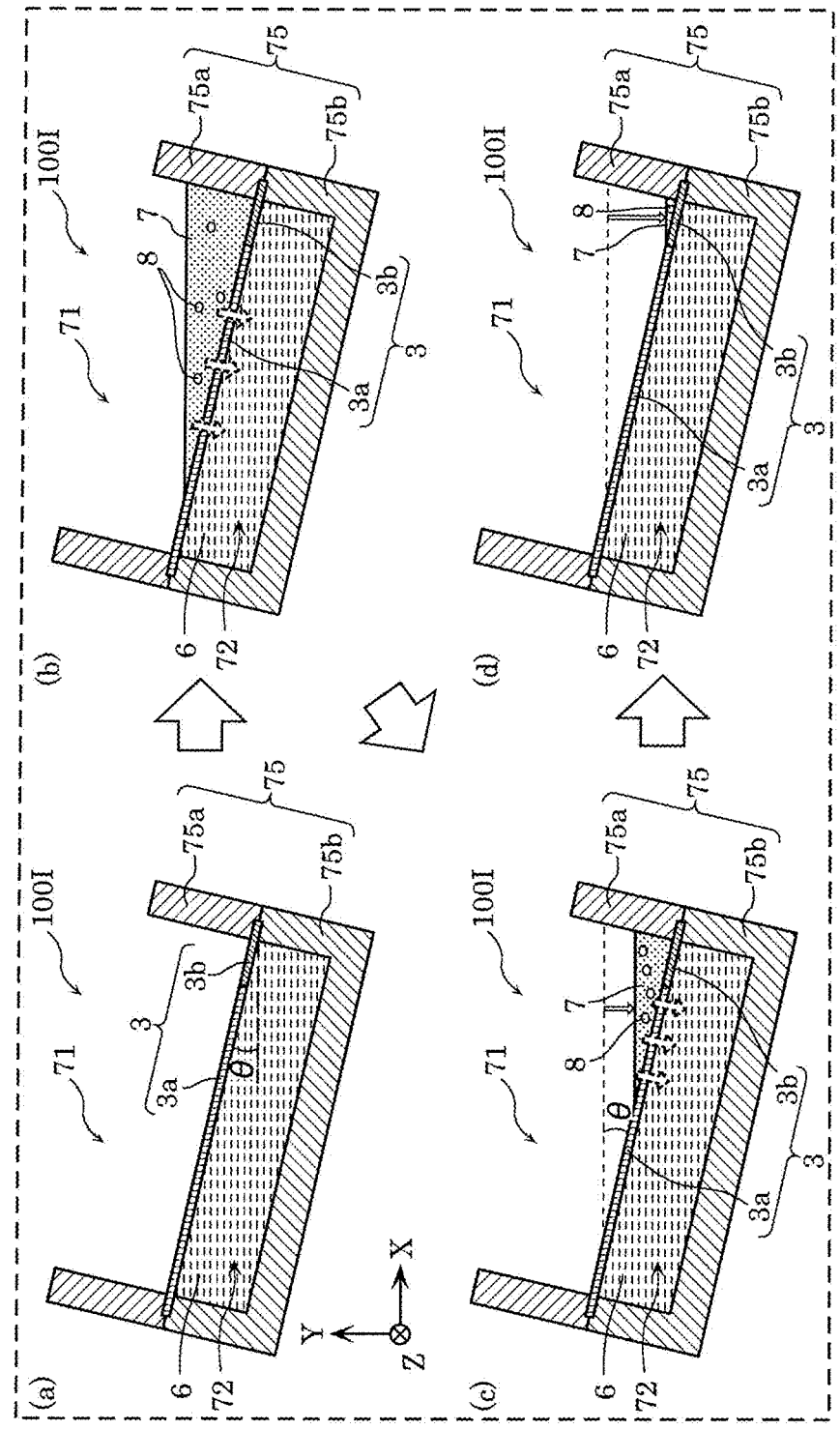
FIG. 16 is a diagram illustrating a process of another method of concentration.

A concentration device according to Embodiment 4 will be described. FIG. 14 is a top view of concentration device 100I according to the present embodiment. FIG. 15 is a schematic cross-sectional view taken along the line XV-XV in FIG. 14. FIG. 16 is a diagram illustrating a process of another method of concentration.

Concentration device 100I according to the present embodiment differs from the concentration devices in the above-described embodiments and their variations in that film 3 is positioned parallel to the bottom of chamber 75.

[Configuration of Concentration Device]

As illustrated in FIG. 14 and FIG. 15, in concentration device 100I, film 3 is positioned to vertically separate the space of chamber 75 having the bottom below. Film 3 is positioned parallel to the bottom of chamber 75.

Film 3 has first region 3a and second region 3b as in Embodiment 1. First region 3a is semipermeable in that first region 3a is permeable to a solvent of a solution, but impermeable to one or more biological substances and drawing agent 6. Second region 3b is impermeable to the solution, the biological substances, and drawing agent 6.

As illustrated in FIG. 16, concentration device 100I is positioned such that film 3 is inclined with respect to the surface of the solution when the solution containing one or more biological substances is introduced into first chamber 75a. Here, the inclination angle of film 3 with respect to the surface of the solution is set to θ degrees. Accordingly, because film 3 is positioned to incline with respect to the surface of the solution, the contact area between the solution and film 3 increases. Thus, the area of the solution in contact with first region 3a of film 3 increases, thereby increasing the concentration efficiency of the solution.

Furthermore, second region 3b is positioned below first region 3a with respect to the surface of the solution. Accordingly, when second region 3b, which is impermeable, is positioned below first region 3a and the surface of the solution reaches second region 3b as the concentration proceeds, the concentration of the solution stops. Therefore, this suppresses depletion of the solution.

With this structure, concentration device 100I according to the present embodiment efficiently concentrates a solution containing one or more biological substances.

Note that, for all the embodiments and their variations described above, the configuration may be applied in which the film is positioned parallel to the bottom of the chamber and such that the film inclines with respect to the surface of the solution when the solution is introduced into the first chamber.

[Method of Concentrating Solution]

Next, a method of concentrating a solution using concentration device 100I according to the present embodiment will be described with reference to FIG. 16.

As illustrated in (a) in FIG. 16, after second chamber 75b of concentration device 100I is filled with drawing agent 6, concentration device 100I is positioned such that film 3 inclines θ degrees with respect to the surface of solution 7 (see (b) in FIG. 16). Then, as shown in (b) in FIG. 16, solution 7 containing one or more biological substances 8 is introduced into first chamber 75a. At this time, when concentration device 100I has a lid, solution 7 may be introduced from the inlet of the lid. When concentration device 100I does not have a lid, a covering component may be placed on the opening of first chamber 75a after solution 7 is introduced into first chamber 75a. Examples of the covering component include materials having forms such as a film, a foil, a sheet, and a plate. Subsequently, as shown in (c) in FIG. 16, the solvent of solution 7 is absorbed into drawing agent 6, which is filled in second chamber 75b via first region 3a of film 3. After that, as illustrated in (d) in FIG. 16, when solution 7 is concentrated to an amount that the surface of solution 7 reaches second region 3b in the top view, solution 7 is less likely to be concentrated because solution 7 is less likely to be in contact with first region 3a. This makes it possible to obtain solution 7 concentrated to a desired concentration rate.

Note that, in the process of the above method of concentration, an example is described in which concentration device 100I is placed with an inclination angle of film 3 of θ degrees after solution 7 is introduced into first chamber 75a. However, concentration device 100I may be inclined after solution 7 is introduced into first chamber 75a.

Furthermore, in the process of the above method of concentration, concentration device 100I may be shaken in the X-axis direction. Here, concentration device 100I may also have a shaker (not illustrated) that shakes solution 7 in the direction in which film 3 inclines. This shakes solution 7 in the inclination direction of film 3, thereby cyclically creating a period in which solution 7 comes into contact with a larger area of first region 3a. This results in a faster concentration of solution 7, which further improves the concentration efficiency of solution 7.

EXAMPLES

The following Examples describe the concentration devices according to the present disclosure in detail, but the present disclosure is not limited to only the following Examples.

Note that in Examples 1 and 2 and Comparative Example 1, concentration devices described below were used to concentrate a biological substance.

[Concentration Device]

Figure 17:
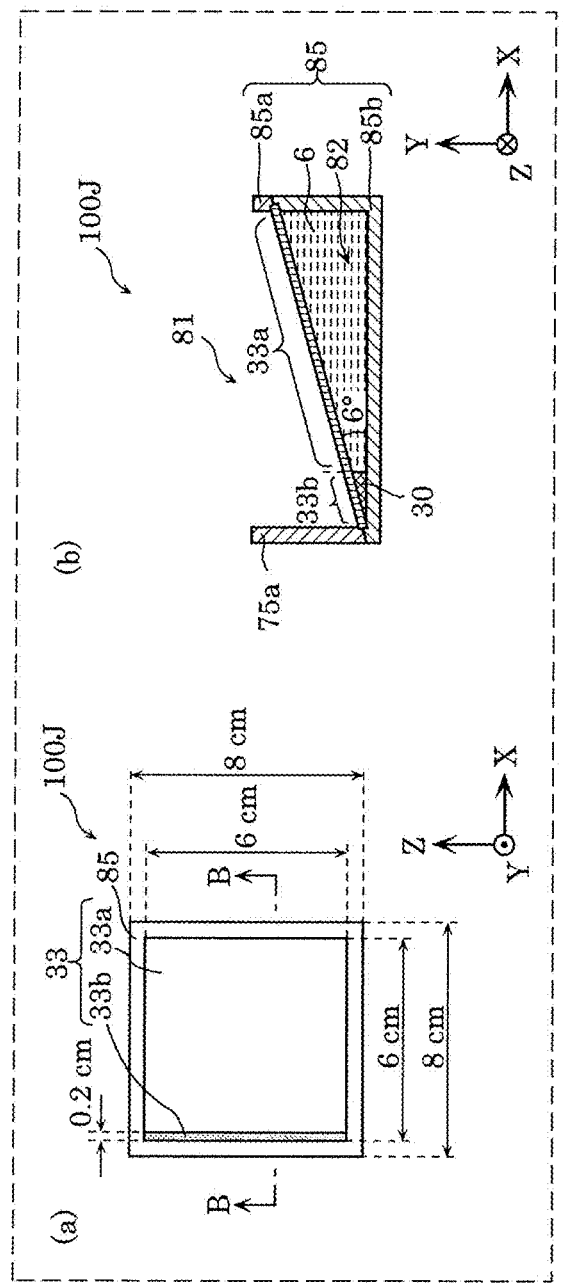
FIG. 17 is a diagram for illustrating the configuration of the concentration device used in Example 1 and Example 2.

FIG. 17 is a diagram for illustrating the configuration of concentration device 100J used in Examples. The (a) in FIG. 17 illustrates a top view of concentration device 100J, and (b) in FIG. 17 illustrates a schematic cross-sectional view taken along the B-B line in (a) in FIG. 17.

As illustrated in (a) in FIG. 17, in concentration device 100J, the shape of chamber 85 is square in the top view. The size of the external shape of chamber 85 is 8 cm long and 8 cm wide, and the size of the inner shape is 6 cm long and 6 cm wide.

As film 33, a cellulose membrane having a molecular weight cutoff (MWCO) of 3.5 K was used, and positioned with an inclination angle $\theta=6°$.

As illustrated in (b) in FIG. 17, in concentration device 100J, second region 33b is a region where prevention component 30 is in contact with film 33, and first region 33a is a region where prevention component 30 is not in contact with film 33.

Prevention component 30 was formed by inserting an acrylic resin into space 82 of second chamber 85b.

Polyethylene glycol (PEG) powder having a molecular weight of 20K was used as drawing agent 6 and filled into second chamber 85b.

[Biological Substance]

As a biological substance, bovine serum albumin (BSA) having a molecular weight of 66 kDa was used. A BSA buffer solution of 50 µg/ml was used as a solution containing the biological substance (hereinafter referred to as a "sample").

[Method of Quantifying Biological Substance]

Figure 18:
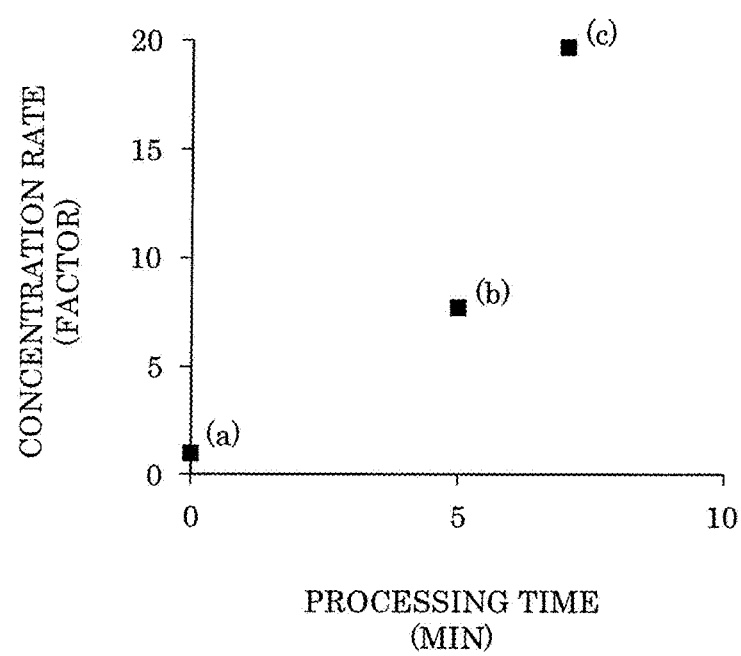
FIG. 18 is a graph showing relationships between the concentration time and the concentration rate of the samples obtained in Example 1, Example 2, and Comparative Example 1.

The amount of the biological substance (BSA) contained in each of the samples obtained in Examples 1 to 2 and Comparative Example 1 was quantified by a colorimetric determination method (the bicinchoninic acid (BCA) assay). BCA was added to the samples, and the samples were reacted for 30 minutes by keeping an incubator at 37° C. After that, the absorbance of 562 nm was measured using the UV spectral measurement, and the biological substance (BSA) in each of the samples was quantified. The results are shown in FIG. 18.

[Method of Detecting Biological Substance]

Figure 19:
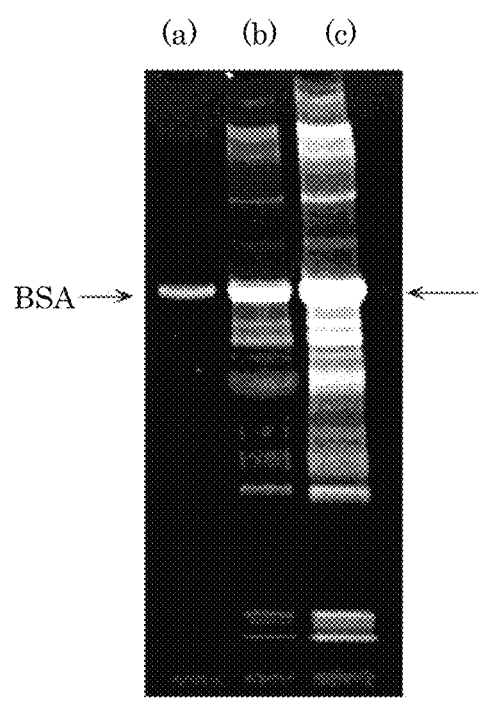
FIG. 19 shows results of sodium dodecyl sulfate polyacrylamide gel electrophoresis (SDS-PAGE) of samples obtained in Example 1, Example 2, and Comparative Example 1.

The biological substance (BSA) in the samples obtained in Examples 1 and 2 and Comparative Example 1 were analyzed by the sodium dodecyl sulfate-polyacrylamide gel electrophoresis (SDS-PAGE) and stained with Oriole Fluorescent Gel Stain (produced by Bio-Rad). The results are shown in FIG. 19.

Example 1

A BSA buffer solution of 50 µg/ml was introduced into first chamber 85a of concentration device 100J, and concentration device 100J was placed still for 5 minutes. The BSA buffer solution was then collected from first chamber 85a, and the BSA was quantified and detected using the method described above.

Example 2

Except for placing the concentration device still for 7 minutes, the same process was performed as in Example 1.

Comparative Example 1

BSA was quantified and detected using an unconcentrated BSA buffer solution.

[Results]

1) Quantification of BSA

FIG. 18 is a graph showing relationships between the concentration time and the concentration rate of the samples obtained in Example 1, Example 2, and Comparative Example 1. As plotted in FIG. 18, (a), (b), and (c) respectively show the results of Comparative Example 1, Example 1, and Example 2.

As shown in FIG. 18, the amount of BSA in each of the samples obtained in Example 1 and Example 2 was significantly increased compared with the amount of BSA of the unconcentrated BSA buffer solution in Comparative Example 1. In Example 1, the concentration rate was higher by a factor of 7 than in Comparative Example 1. In Example 2, the concentration rate was higher by a factor of 20 than in Comparative Example 1. Note that the volume of the samples decreased with the concentration time.

2) Detection of BSA

FIG. 19 shows results of SDS-PAGE of the samples obtained in Example 1, Example 2, and Comparative Example 1.

The (a), (b), and (c) in FIG. 19 respectively show the fluorescence images obtained by separating the biological substance from each of the samples in Comparative Example 1, Example 1, and Example 2 by SDS-PAGE and stained with a fluorescent dye.

As shown in FIG. 19, a clearer band of fluorescence was shown as the concentration time increased. Accordingly, the concentration devices according to the present disclosure efficiently concentrate a minute amount of the biological substance included in the biological samples in a shorter time.

Although the concentration devices according to the present disclosure have been described based on the embodiments and their variations, the present disclosure is not limited to the above-described embodiments and variations. The scope of the present disclosure also includes various modifications of the embodiments and their variations that are conceivable by those skilled in the art, and other embodiments that can be constructed by combining part or some of the structural elements in the embodiments and the variations without departing from the scope of the present disclosure.

INDUSTRIAL APPLICABILITY

The concentration devices according to the present disclosure efficiently concentrate a solution containing one or more biological substances. The concentration devices according to the present disclosure can also be used as a test kit for examining a biological condition, because they are easy to be implemented without special operations.

The invention claimed is:

1. A concentration device that concentrates a solution containing a biological substance, the concentration device comprising:
   a bottom;
   a first chamber into which the solution is to be introduced;

a second chamber to be filled with a drawing agent; and a film that separates a space of the first chamber and a space of the second chamber, wherein:

the film has a first region and a second region, the first region is semipermeable in that the first region is permeable to a solvent of the solution but impermeable to the biological substance and the drawing agent, the second region is impermeable to the solution, the biological substance, and the drawing agent, the film is positioned to incline with respect to the bottom of the concentration device, and the second region is positioned below the first region with respect to the bottom of the concentration device.

2. The concentration device according to claim 1, wherein the film has an external shape when viewed from a direction perpendicular to the bottom, and the external shape includes a plurality of sides, the first region is formed by sides among the plurality of sides and a boundary between the first region and the second region, the second region is formed by sides among the plurality of sides and the boundary between the first region and the second region, and each of the sides forming the second region is shorter than any one of the sides forming the first region.

3. The concentration device according to claim 2, wherein the external shape of the film is trapezoidal.

4. The concentration device according to claim 1, wherein the film has an axis of symmetry perpendicular to the bottom the first region and the second region are symmetrically positioned with respect to the axis of symmetry.

5. The concentration device according to claim 1, further comprising:

a carrier that is placed on the second region in the first chamber and carries the biological sub stance.

6. The concentration device according to claim 5, wherein the carrier is a porous material.

7. The concentration device according to claim 6, wherein the porous material is cellulose.

8. The concentration device according to claim 1, wherein, the drawing agent is liquid.

9. The concentration device according to claim 1, wherein, the drawing agent is powder.

10. The concentration device according to claim 1, further comprising:

a shaker that shakes the solution in a direction in which the film inclines.

11. The concentration device according to claim 5, further comprising:

an analyzer that separates the biological substance using the carrier.

12. The concentration device according to claim 1, wherein the first region and the second region are disposed adjacent to each other when viewed from a direction perpendicular to the bottom.

13. The concentration device according to claim 1, wherein the first region and the second region can be seen from a top view of the concentration device.

\* \* \* \* \*